United States Patent
Shchervinsky et al.

(10) Patent No.: US 6,254,425 B1
(45) Date of Patent: Jul. 3, 2001

(54) ELECTRICAL CONNECTOR FOR CARDIAC DEVICES

(75) Inventors: Semyon Shchervinsky, Whitehouse Station; Claude O. Clerc; Alex Ilori, both of Flemington, all of NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/451,591

(22) Filed: Nov. 30, 1999

(51) Int. Cl.[7] .................................................. H01R 11/00
(52) U.S. Cl. ........................ 439/502; 439/505; 439/169; 128/404; 607/104
(58) Field of Search ..................... 439/502, 505, 439/169; 128/404, 414, 419 P, 784, 385; 607/104, 119, 129

(56) References Cited

U.S. PATENT DOCUMENTS

| | | | |
|---|---|---|---|
| 4,010,756 | 3/1977 | DuMont et al. | 128/404 |
| 4,341,226 | 7/1982 | Peters | 128/784 |
| 4,442,840 | 4/1984 | Wojciechowicz, Jr. | 128/419 |
| 4,541,440 | 9/1985 | Parsonnet | 128/785 |
| 4,633,880 | 1/1987 | Osypka et al. | 128/642 |
| 4,693,258 | 9/1987 | Osypka et al. | 128/783 |
| 5,217,027 | 6/1993 | Hermens | 128/784 |
| 5,241,951 | 9/1993 | Mason et al. | 607/104 |
| 5,241,957 | 9/1993 | Camps et al. | 607/119 |
| 5,314,463 | 5/1994 | Camps et al. | 607/129 |
| 5,366,496 | * 11/1994 | Dahl et al. | 607/116 |
| 5,547,399 | * 8/1996 | Naghi et al. | 439/623 |
| 5,632,770 | * 5/1997 | Schaldach | 607/122 |
| 5,702,270 | 12/1997 | Casica et al. . | |
| 5,792,217 | 8/1998 | Camps et al. | 607/119 |
| 5,795,178 | 8/1998 | Schilder et al. | 439/417 |

* cited by examiner

Primary Examiner—Gary F. Paumen
Assistant Examiner—Alexander Gilman

(57) ABSTRACT

A temporary cardiac pacing wire, or a similar device, includes a pair of flexible electrode wires extending conjointly from a distal end of the pacing wire to its proximal end, where two electrically conductive sections are located. The conductive sections are suitable for connection to a power source adapted to generate electrical signals for stimulating, pacing, sensing, monitoring or defibrillating the heart of a patient. One conductive section results from the distal end of a Keith-type needle that breaks away from the rest of the needle. The other conductive section is arranged at the free end of a third electrode wire which is movable independently of the other two electrode wires, thereby permitting its connection to the power source in a plug-like fashion.

12 Claims, 4 Drawing Sheets

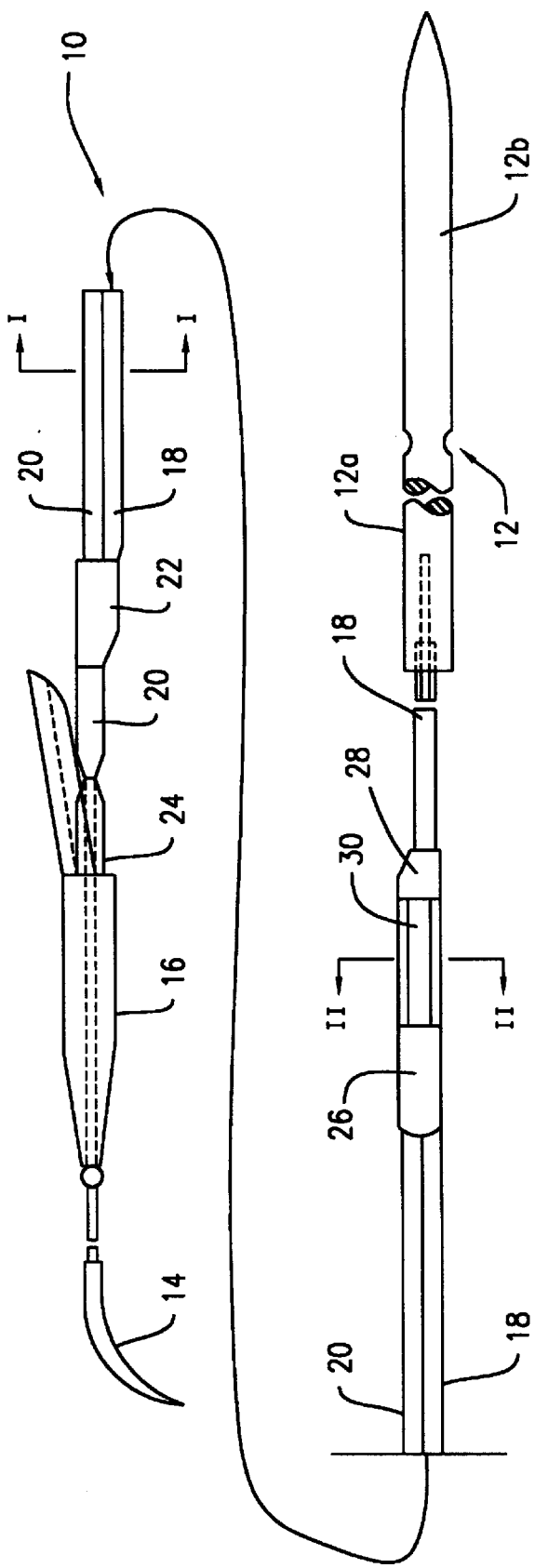
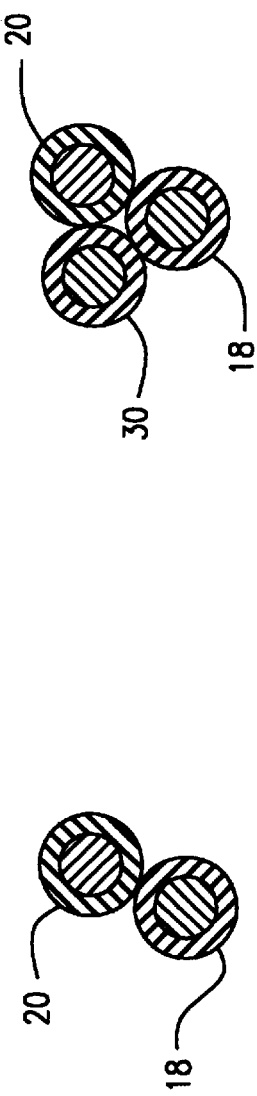
FIG. 1
FIG. 1A
FIG. 1B

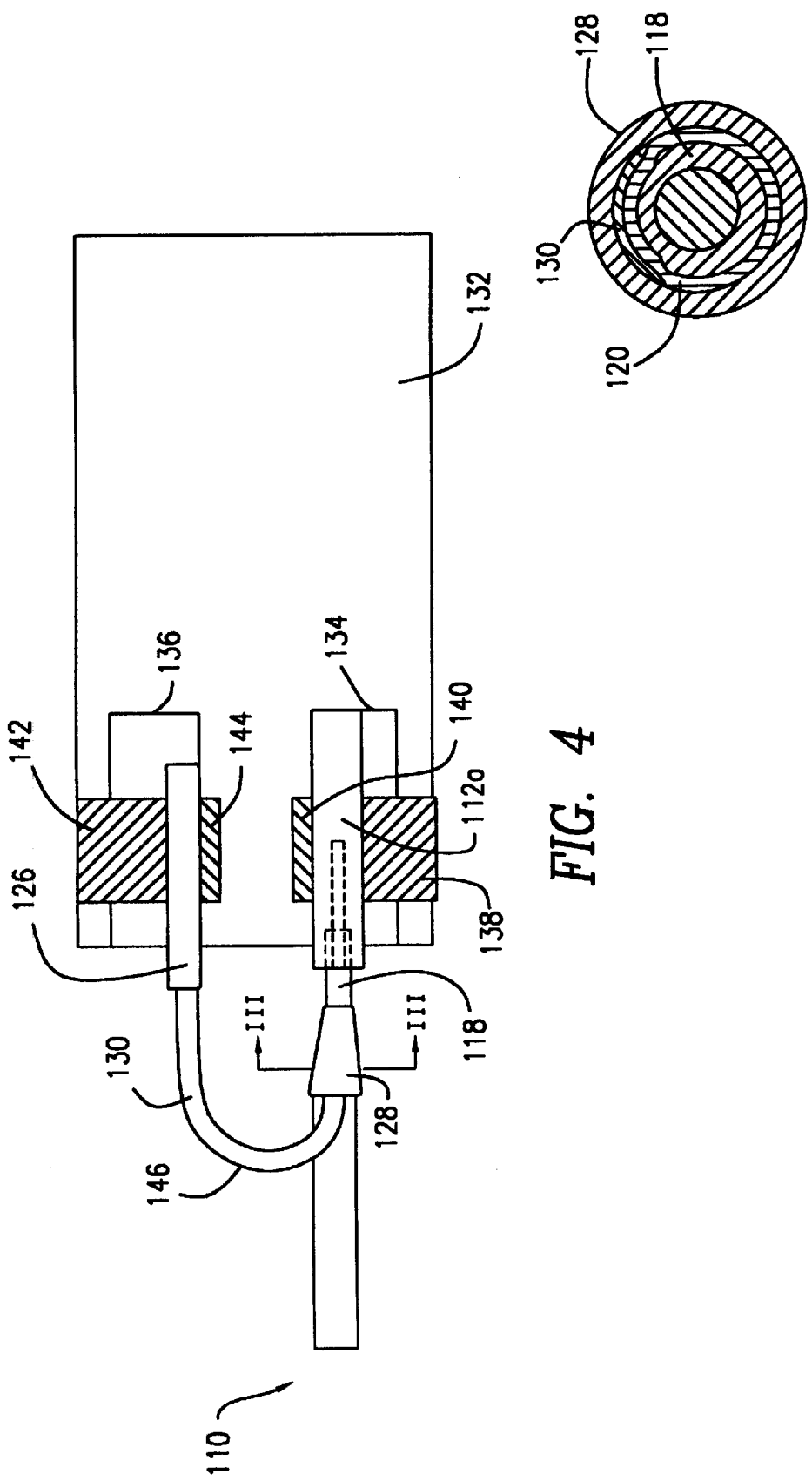

ELECTRICAL CONNECTOR FOR CARDIAC DEVICES

FIELD OF THE INVENTION

The present invention relates to electrical connectors for cardiac devices and, more particularly, to temporary cardiac pacing wires that are adapted for use with apparatus that generate electrical signals suitable for stimulating, pacing, sensing, monitoring or defibrillating the heart.

BACKGROUND OF THE INVENTION

Devices to stimulate or regulate cardiac function have been known and used for decades. They involve a power source (pacemaker) and one or more surgical electrodes to attach the source to the heart. They are generally of two types.

Implantable pacers are intended for long-term use and, as the name suggests, are entirely implanted in the body. The other type is intended for temporary use. The temporary pacemaker is located outside the body and is connected to the heart by a surgical electrode called a "temporary pacing wire." Although surgical electrodes are used for preparing electrocardiograms and other applications, for the sake of brevity, the description that follows is focused on temporary pacing wires.

In general, such wires are constructed of a number of fine, stainless steel wires braided or twisted together to form a single, flexible, multi-strand electrode wire. The major portion of the wire is electrically insulated with a polyethylene, polytetrafluoroethylene, silicon, nylon, or another non-conducting coating, with a short length of wire at either end left uninsulated. To the distal uninsulated end of the electrode wire there is attached, by swaging or other means, a fine curved needle for piercing the heart tissue to place the uninsulated end of the electrode in the myocardium. At the proximal end of the electrode wire, a straight (e.g., Keith-type) cutting needle is attached for piercing the thoracic wall to lead the electrode to an outer point for connection with the pacemaker. Once that has been accomplished, the needle, or its sharp-pointed end, is clipped or broken off and the proximal end of the electrode is readied for attachment to the pacemaker as required to stimulate or regulate the beating of the heart. A single setup involves two electrodes, i.e., two temporary pacing wires. During the time that the temporary pacing wire is performing its function, the unsinsulated end of the electrode must remain anchored in the myocardium. The anchorage must be secure, lest the continually beating heart cause the wire to be expelled from the myocardium. When the need for the pacing wire has passed, it is necessary to remove from the body the wire that runs from the external pacemaker to the myocardium.

The process of preparing the proximal ends of the pacing wires (electrodes) to the pacemaker requires numerous steps and is time consuming. Not only do the proximal ends of the pacing wires require removal from the Keith-like needles, but separate steps are required to make them suitably adapted for attachment to electrodes (terminals) within the pacemaker.

DESCRIPTION OF THE RELATED ARTS

U.S. Pat. No. 4,693,258, issued on Sep. 15, 1987 to Osypka et al., discloses an electrode connector assembly that can be used to electrically connect the proximal end of a pacing wire (with insulation removed) to the socket of a pacing or monitoring instrument. This approach is useful but requires many small parts to be assembled. This may prove to be difficult and time consuming to work with in the operating room environment. Also, multistrand wires have a tendency to fray which adds to difficulties. Additionally, small parts are prone to be easily lost.

U.S. Pat. No. 4,633,880, issued on Jan. 6, 1987 to Osypka et al., discloses an implantable bipolar electrode assembly where the two distal ends of the wire are received in an electrically conductive sleeve (pole). One wire is in electrical contact with the sleeve and the second wire passes through the sleeve. The distal end of the second wire is stripped of insulation to provide electrical contact with heart tissue. The stripped section is configured to introduce mechanical resistance to its removal from heart tissue. Although this electrode assembly is effective in delivering a bipolar signal to the heart, it is not intended for use as a direct electrical connection with a pacemaker.

U.S. Pat. No. 5,792,217, issued on Aug. 11, 1998 to Camps et al., discloses an arrangement in which the proximal ends of two pacing wires can be simultaneously broken away from a Keith-type needle. Affixed to the proximal end of each wire is an electrical connector that is suitably dimensioned to connect to a pacing or monitoring instrument. This arrangement requires complex manufacturing processes to fabricate. Because the Keith-type needle accommodates two electrical connectors in a side-by-side fashion, the needle is approximately twice as large as those typically used. The larger needle can cause undesirable tissue trauma.

In view of the foregoing, there is a need for a simple, efficient and reliable mechanism for connecting the proximal ends of bipolar temporary pacing wires to a pacing or monitoring instrument. The mechanism should have few parts, be easy to manufacture and be consistent with minimal tissue trauma to the patient.

BRIEF SUMMARY OF THE INVENTION

An object of this invention is to provide a novel and improved surgical electrical connector that can be connected to a medical instrument in a simple and time-saving manner.

Another objective of the invention is to provide an electrical connection that can be electrically connected directly to the socket of a pacing or monitoring instrument.

A further object of the invention is to provide an assembly requiring minimal tissue trauma during installation and simultaneously allowing for two electrical connections to be established with a pacing or monitoring instrument.

An additional object of the invention is to provide an electrical connector with partially insulated ends.

Still another object of the invention is to provide an electrical connector assembly that is smaller in diameter than the Keith-type needle used to guide the connector to the outside of the body.

With the foregoing objects in mind, the present invention relates to an electrical connector assembly in which a branch-like conductive lead is equipped with a connector in such a manner that the connector can be plugged into a socket-like terminal of a power source adapted to generate electrical signals. The present invention is especially suited for use in conjunction with a temporary cardiac pacing wire which includes a pair of electrode wires extending conjointly from a distal end of the pacing wire to its opposite (i.e., proximal) end. One of the electrode wires is mechanically and electrically connected to the distal end of a Keith-type needle that breaks away from the needle, thereby forming another conductive lead adapted for connection to another terminal of the power source in a plug-like fashion. The branch-like conductive lead is mechanically and electrically connected to the other electrode wire such that the branch-like conductive lead is freely movable independently of the pair of electrode wires. In this embodiment, the power source would be a pacing or monitoring instrument which generates electrical signals for stimulating, pacing, sensing, monitoring or defibrillating the heart of a patient. To facilitate its connection to the pacing or monitoring instrument in a plug-like fashion, the connector of the branch-like conductive lead may have a length which is more than ten times the diameter of the Keith-type needle, while having a maximum lateral dimension (e.g., a diameter in the case of a circular cross section) which is smaller than or equal to the diameter of the Keith-type needle.

The invention has the advantage of ease of use without requiring additional pin-plugs or other assemblies. Also, the invention allows the use of needles, wires and connectors sized smaller than or equal to the size of existing Keith-type needles.

BRIEF DESCRIPTION OF THE DRAWINGS

For a better understanding of the present invention, reference is made to the following detailed description of an exemplary embodiment considered in conjunction with the accompanying drawings, in which:

FIG. 1 is a schematic illustration of a first embodiment of the invention showing a bipolar temporary pacing wire including a distal anchoring portion;

FIG. 1A is a cross-sectional view of the embodiment of FIG. 1 taken along section line I—I and looking in the direction of the arrows;

FIG. 1B is a cross-sectional view of the embodiment of FIG. 1 taken along section line II—II and looking in the direction of the arrows;

FIG. 4 is a schematic, partially cross-sectional illustration of a second embodiment of the invention inserted into a pacemaker; and FIG. 4A is a cross-sectional view of the embodiment of FIG. 4 taken along section line III—III and looking in the direction of the arrows.

DETAILED DESCRIPTION OF THE INVENTION

Figure 2:
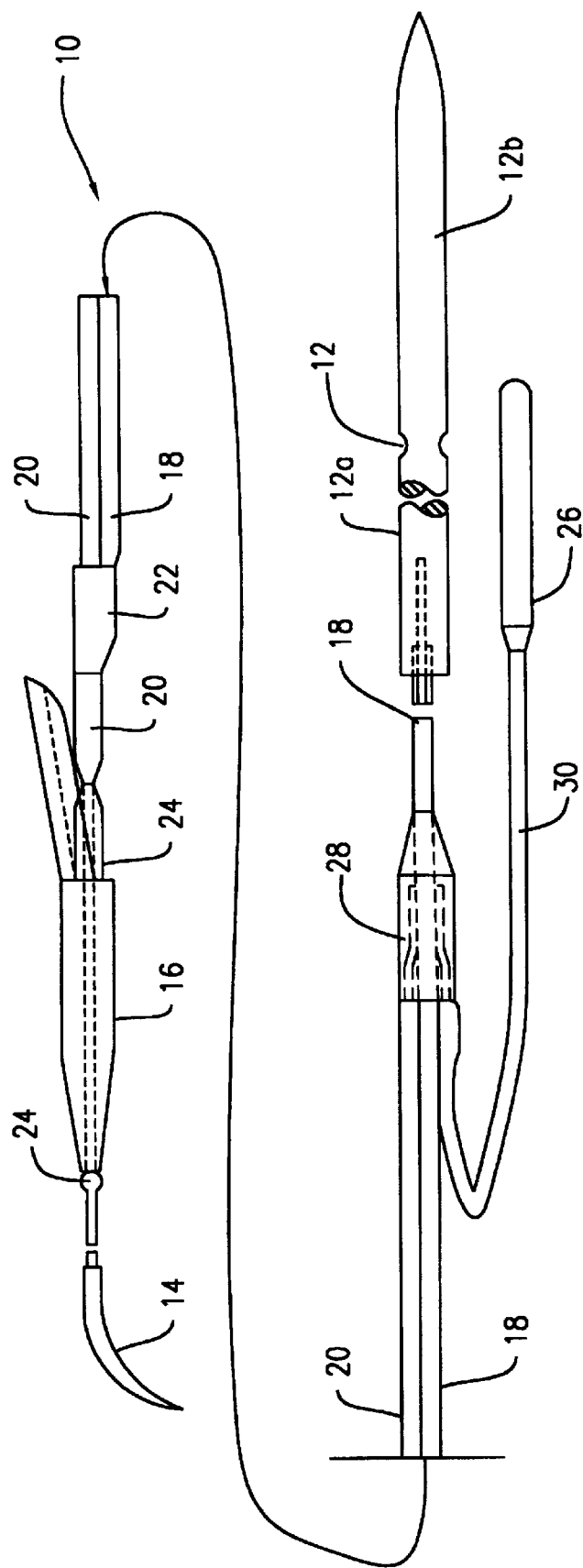
FIG. 2 is a schematic illustration of the embodiment of FIG. 1 viewed from a different perspective.

Although the present invention is applicable to many different types of cardiac devices, it is especially suitable for use in conjunction with a bipolar temporary cardiac pacing wire. Accordingly, the present invention will be described below in connection with such a pacing wire.

As used herein, the term "distal" shall mean that portion of the pacing wire or element thereof which is remote from a source of electric signals located external to the patient's body. Conversely, the term "proximal" shall mean that portion of the pacing wire or element thereof which is in close proximity to the external source of electrical signals.

Referring to FIG. 1, a bipolar temporary cardiac pacing wire 10 includes a Keith-type breakaway needle 12 arranged at a proximal end of the pacing wire 10 and a curved needle 14 arranged at a distal end of the pacing wire 10, which also includes any type of suitable anchor 16 such as the one disclosed in U.S. patent application Ser. No. 09/307,537, which was filed on May 7, 1999 by the assignee of the present application and which is incorporated herein by reference. The Keith-type needle 12, such as the one disclosed in U.S. Pat. No. 4,010,756 issued on Mar. 8, 1977 to DuMont et al., has a distal section 12a and a proximal section 12b, which is pointed for piercing the thoracic wall to lead the proximal end of the pacing wire 10 outside the chest cavity of a patient in accordance with a medical procedure well known in this field. The curved needle 14 is adapted to pierce the heart tissue and to attach the anchor 16 to the heart in accordance with another well-known medical procedure.

A pair of insulated, electrically conductive electrode wires 18, 20 extends between the distal and proximal ends of the pacing wire 10. The electrode wires 18, 20 are of the "lamp cord" type (i.e., they are arranged in a side-by-side fashion as shown in FIG. 1A), each wire having a braided, multi-strand core of stainless steel and a surrounding layer of insulation made from polyethylene. Alternatively, the core of each wire could have a twisted construction with a surrounding layer of insulation made from polyethylene or any other suitable electric non-conducting material, such as silicon, polytetrafluoroethylene, or nylon.

At the distal end of the pacing wire 10 there are two electrodes 22, 24. The electrode 22 is electrically and mechanically connected to the electrode wire 18, but only mechanically connected to the electrode wire 20, which passes through the sleeve-like electrode 22 and is mechanically and electrically connected to the electrode 24. The electrodes 22, 24 have a conventional construction and are adapted to transmit electrical signals from one to the other for the purpose of stimulating, pacing, sensing, monitoring, or defibrillating the heart.

An elongated connector 26 and a bushing-like connector 28 are located at the proximal end of the pacing wire 10. The connector 26 is mechanically and electrically connected to a free end of a third electrode wire 30, which has a construction similar to that of the electrode wires 18, 20. The other end of the electrode wire 30 is mechanically connected to the connector 28, which extends circumferentially about all three of the electrode wires 18, 20, 30 (see FIG. 2). While the connectors 26, 28 have a generally circular cross-sectional shape (see, for example, the corresponding connectors 126, 128 in FIG. 4A), they could have other cross-sectional shapes, such as oval, square, rectangular, etc.

Within the connector 28, the electrode wire 30 is electrically connected to the electrode wire 20, but not to the electrode wire 18 or to the connector 28, which can therefore be made from an electrically non-conductive material. If the connector 28 is used to electrically connect the electrode wires 20, 30, then it would have to be made from suitable electrically conductive material, in which case electrical insulation could be applied to avoid shorting. The majority of the electrode wire 30 is not attached to either of the electrode wires 18, 20; and it is, therefore, free for movement independently of the rest of the pacing wire 10 (see FIG. 2).

The electrode wire 18 is only mechanically connected to the connector 28. In fact, the wire electrode 18 is electrically insulated from the electrode wires 20, 30, as well as the connector 28. Thus, the electrode wire 18 is only electrically connected to the electrode 22 (at one end of the wire 18) and to the distal section 12a of the Keith-type needle 12 (at an opposite end of the wire 18).

Figure 3:
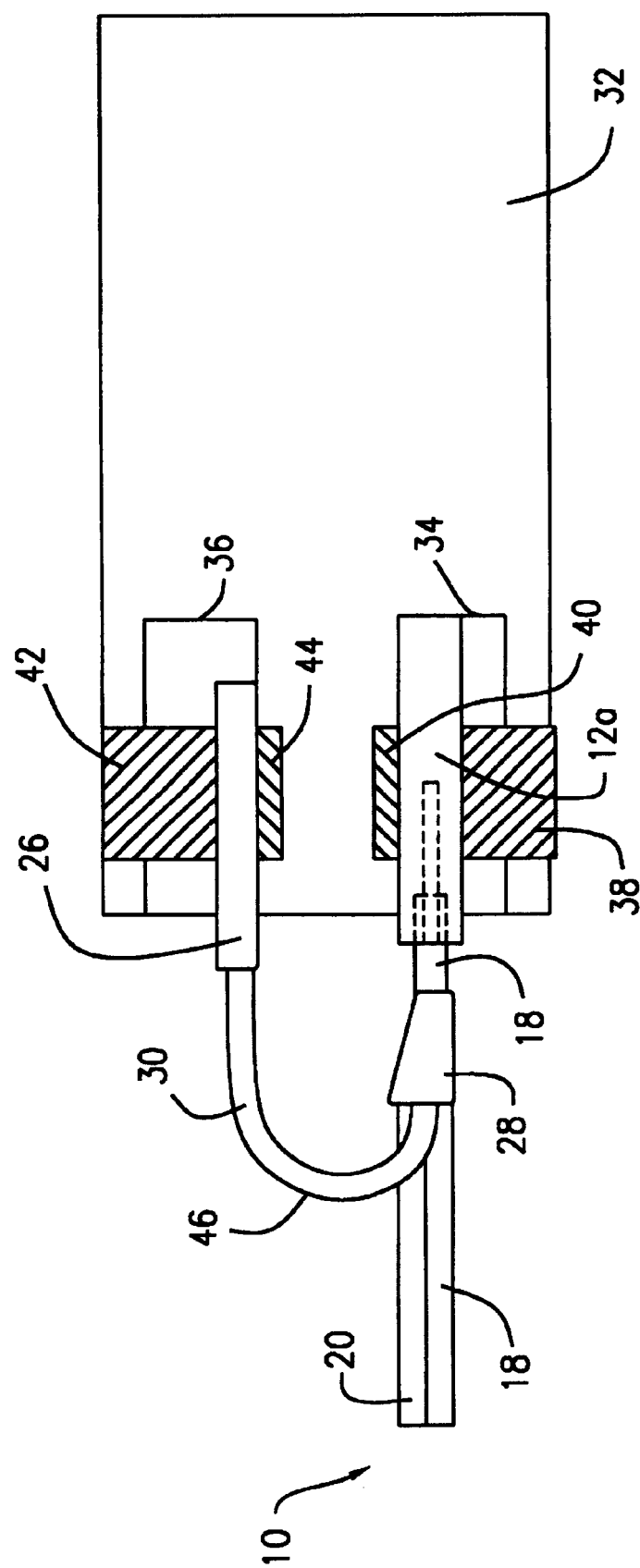
FIG. 3 is a schematic, partially cross-sectioned illustration of the embodiment of FIGS. 1 and 2 inserted into a pacemaker.

Referring now to FIG. 3, the pacing wire 10 is shown adapted for use in connection with a pacemaker 32 which has a pair of sockets 34, 36. As is typical of pacemakers like the pacemaker 32, a pair of spring-loaded clamps 38, 40 is mounted in the socket 34, one of which carries an electrical charge (either positive or negative) and the other of which is neutral (it does not carry either a positive charge or a negative charge). In a similar and typical fashion, a pair of spring-loaded clamps 42, 44 is mounted in the socket 36, one of which is neutral and the other of which carries an electrical charge opposite the charged clamp in the socket 34 (e.g., if the charged clamp in the socket 34 carries a negative charge, then the charged clamp in the socket 36 carries a positive charge, and vice versa). Alternatively, the pacemaker 32 could be the type (e.g., a Medtronic Model No. 5375) in which all of the clamps (i.e., the clamps 38, 40 of the socket 34 and the clamps 42, 44 of the socket 36) carry an electric charge.

In order to make an electrical connection within the socket 34 of the pacemaker 32, the Keith-type needle 12 is severed intermediate to its ends and the distal section 12a is inserted into the socket 34, while the proximal end 12b is discarded. Inside the socket 34, the distal section 12a is gripped between the clamps 38, 40 which have concave-shaped gripping surfaces so as to make good electrical and/or mechanical contact with the cylindrically-shaped distal section 12a and hence the electrode wire 18. Because the distal section 12a is made entirely of an electrically conductive material, such as stainless steel, electric-conducting contact within the socket 34 is ensured, regardless of which of the clamps 38, 40 is charged and regardless of how the distal section 12a is oriented relative to the charged clamp.

In order to make an electrical connection within the socket 36 of the pacemaker 32, the connector 26 is simply inserted, in a plug-like fashion, into the socket 36, where it is gripped between the clamps 42, 44 which have concave-shaped gripping surfaces to ensure good electrical and/or mechanical contact with the cylindrically-shaped connector 26 and hence the electrode wire 30. Because the connector 26 is cylindrical and is made from an electrically conductive material, such as stainless steel, electric-conducting contact within the socket 36 is ensured, regardless of which of the clamps 42, 44 is charged and regardless of how the connector 26 is oriented relative to the charged clamp. The electrode wire 30 is long enough and flexible enough to form a loop 46 in the segment extending from the connector 26 to the connector 28, where the electrode wire 30 is electrically connected to the electrode wire 20.

While the actual length of the connector 26 needs only be sufficient to assure secure insertion into the socket 36 of the pacemaker 32, preferably this length is about ten times or greater than ten times the diameter of the Keith-type needle 12. It is also preferable that the connector 26 has a diameter which is smaller than or equal to that of the Keith-type needle 12. If the connector 26 does not have a circular cross-sectional shape, then its maximum lateral dimension would preferably be smaller than or equal to the diameter of the Keith-type needle 12. The diameter or maximum lateral dimension of the connector 26 could, however, be larger than the diameter of the Keith-type needle 12.

The connector 26 is fabricated from a solid piece of stainless steel wire which is drilled from its back side so as to form a blind hole. After inserting an uninsulated end of the electrode wire 30 into the blind hole, the connector 26 is mechanically and electrically attached to the electrode wire 30 by a swaging operation.

If the connector 28 is made from an electric insulating material, such as polypropylene or polyethylene, it can be applied to the electrode wires 18, 20, 30 by any conventional process. If the connector 28 is made from an electric conducting material, such as stainless steel, it would be swaged to the electrode wires 18, 20, 30 and then coated with a layer of insulation.

What follows is a description of an alternate embodiment of the present invention. In describing this embodiment, elements corresponding to elements described above in connection with the embodiment of FIGS. 1–3 will be described by corresponding reference numerals increased by one hundred. The alternate embodiment is constructed and operates in the same manner as the embodiment of FIGS. 1–3, unless otherwise specified.

In the embodiment of FIGS. 4 and 4A, the electrode wires 118, 120 have a coaxial construction (see FIG. 4A). Except for the size and shape of the connector 128, the other components of the pacing wire 110 are essentially the same as their counterparts in the embodiment of FIGS. 1–3. To form the desired electrical connection between the electrode wire 120 and the electrode wire 130, insulation is removed from portions of both of the wires and the exposed electric conducting cores are then subjected to a swaging operation, resulting in the assembly illustrated in FIG. 4A.

It will be understood that the embodiments described herein are merely exemplary and that a person skilled in the art may make many variations and modifications without departing from the spirit and scope of the invention. All such variations and modifications are intended to be included within the scope of the invention as defined in the appended claims.

What is claimed is:

1. An electrical connector for a cardiac device, comprising wire means, including at least a pair of electrically conductive wires; and connecting means for electrically connecting said wire means to the cardiac device, said connecting means including another electrically conductive wire, a first connector in the form of a sleeve which is sized and shaped for insertion into a socket-like electrical terminal and which is mechanically and electrically connected to said another wire, a second connector which is mechanically connected to said at least a pair of wires and to said another wire, said another wire being electrically connected to one of said at least a pair of wires within said second connector and being moveable independently of said at least a pair of wires such that said first connector can be plugged into a socket-like electrical terminal, and a distal portion of a severed Keith-type needle, said distal portion being mechanically and electrically connected to another one of said at least a pair of wires.

2. An electrical connector according to claim 1, wherein said second connector is made from an electrically non-conductive material.

3. An electrical connector according to claim 1, wherein said second connector is made from an electrically conductive material having an electrically insulated exterior surface.

4. An electrical connector according to claim 1, wherein said Keith-type needle has an outside diameter and said first connector has a length which is at least about ten times said diameter of said Keith-type needle.

5. An electrical connector according to claim 1, wherein said first connector has a cylindrical shape and includes a blind bore which is sized and shaped to receive an uninsulated end of said another wire.

6. An electrical connector according to claim 1, wherein said at least a pair of wires includes a plurality of wires arranged in a side-by-side fashion relative to each other.

7. An electrical connector according to claim 1, wherein said at least a pair of wires includes a plurality of wires arranged coaxially relative to each other.

8. An electrical connector according to claim 1, wherein said second connector has a bushing-like shape.

9. An electrical connector according to claim 8, wherein said second connector extends circumferentially about said at least a pair of wires and said another wire.

10. An electrical connector according to claim 1, wherein said wire means further includes at least a pair of electrodes at a distal end of said at least a pair of wires.

11. An electrical connector according to claim 10, wherein said another wire is connected to said one wire at a proximal end of said at least a pair of wires.

12. A temporary pacing wire, comprising a first electrode at a distal end of said pacing wire; a second electrode at said distal end of said pacing wire; a first electrically conductive wire electrically connected to said first electrode and extending from said first electrode to a proximal end of said pacing wire; a second electrically conductive wire electrically connected to said second electrode and extending from said second electrode to said proximal end of said pacing wire; first connecting means, located at said proximal end of said pacing wire, for electrically connecting said first wire to a source of electric signals, said first connecting means including a distal portion of a severed Keith-type needle that is mechanically and electrically connected to said first wire; and second connecting means, located at said proximal end of said pacing wire, for electrically connecting said second wire to a source of electrical signals, said second connecting means including a first connector mechanically connected to said first and second wires, a third electrically conductive wire mechanically connected to said first connector and electrically connected to said second wire, and a second connector mechanically and electrically connected to said third wire, said second connector being sized and shaped for insertion into a socket-like electrical terminal.

* * * * *